United States Patent [19]

Scott

[11] Patent Number: 4,537,187

[45] Date of Patent: Aug. 27, 1985

[54] EARPLUG

[76] Inventor: Robert T. Scott, 416 Lighthouse Ave., Santa Cruz, Calif. 95060

[21] Appl. No.: 539,483

[22] Filed: Oct. 6, 1983

[51] Int. Cl.³ .................................. A61F 11/02
[52] U.S. Cl. .................................................. 128/151
[58] Field of Search ............... 128/132 R, 151, 152

[56] References Cited

U.S. PATENT DOCUMENTS

| 2,717,596 | 9/1955 | Knight | 128/152 |
| 2,737,953 | 3/1956 | Wiltein | 128/152 |
| 2,881,759 | 4/1959 | Hocks et al. | 128/152 |
| 3,047,089 | 7/1962 | Iwislocki | 128/151 |
| 3,565,069 | 2/1971 | Miller | 128/152 |
| 3,782,379 | 1/1974 | Lampe | 128/152 |
| 4,353,364 | 10/1982 | Woods | 128/152 |

FOREIGN PATENT DOCUMENTS 320282  12/1971  U.S.S.R. .................. 128/151

Primary Examiner—John D. Yasko
Assistant Examiner—Christa K. Scott
Attorney, Agent, or Firm—Robert G. Slick

[57] ABSTRACT

An earplug particularly adapted for use by surfers and swimmers is provided having a small hole therein which keeps out water but which allows the user to hear, said plug being made of a soft plastic having a density of less than 1 whereby said plug will float.

2 Claims, 4 Drawing Figures

//  4,537,187

EARPLUG

SUMMARY OF THE INVENTION

The present invention relates to an improved form of earplug. The earplug of the present invention was developed primarily for surfers to prevent the development of bony stenosis of the external auditory canal due to diffuse exostoses; it also has proved useful for patients with otitis externa and chronic otitis media; and it also prevents ruptured eardrums.

The plugs are made of soft plastic molded to fit the cavum conchae and have an extension to fit behind the crus helicis.

A unique feature of the plug is a small opening in the portion occluding the meatus. This fenestration is small enough to keep water out of the ear in most instances but large enough to result in little sound attenuation (5 dB or less). As such, it is acceptable to swimmers, surfers, and lifeguards who must keep water out of their ears but wish to have unimpaired hearing.

The advantages of the plug are many: they do not require preparation of a special mold for the patient and, as such, are inexpensive and readily available. The soft plastic of which they are made prevents injury if the user should receive a blow to the ear. The fenestration allows the wearer to hear well and the wearer can equalize pressures under water as in scuba activity.

A further advantage of the plug of the present invention is that it has a density less than water, so that it floats. This is particularly advantageous for swimmers and surfers.

Various other objects and features of the invention will be brought out in the balance of the application.

DESCRIPTION OF THE PREFERRED EMBODIMENT

Figure 1:
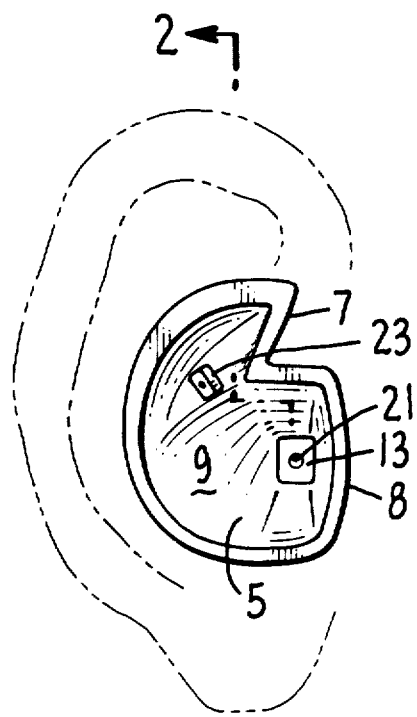
FIG. 1 is an end view from the outside of a plug embodying the present invention.
Figure 2:
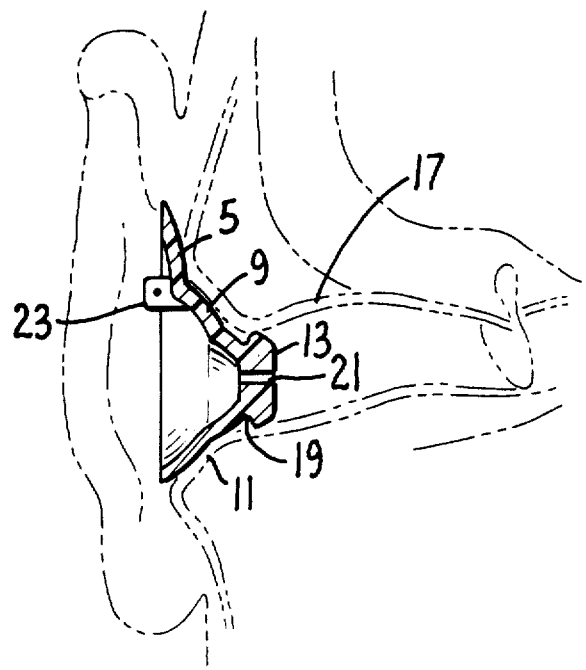
FIG. 2 is a section on the line 2—2 of FIG. 1.
Figure 3:
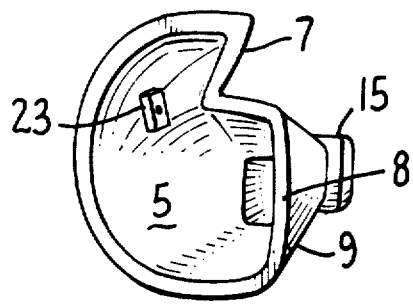
FIG. 3 is a front perspective view of the plug.
Figure 4:
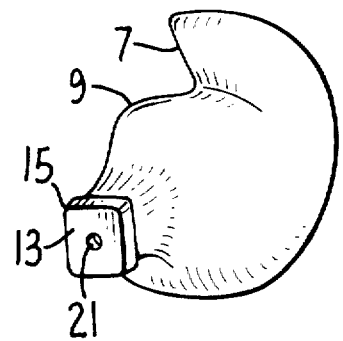
FIG. 4 is a rear perspective view of the plug.

In the drawings forming a part of this application, the plug of the present invention is shown in solid lines while the ear of a user is shown in phantom. Thus, referring to the drawings by reference characters, the plug of the present invention has an external flange 5 extending against the pinna and with a side 7 adapted to fit against the helix and a side 8 adapted to fit against the tragus. The plug has a conical portion 9 adapted to fit against the cavum concha 11. At the inner end of the plug is a flat portion 13 having a small external flange 15 thereon which fits into the auditory canal 17 and tends to grip the side of the auditory canal as is shown at 19. At the center of the flat portion 13 is a small fenestration 21. This fenestration is selected to be of such a size that it will normally keep out water, yet will offer little sound attenuation. It has been found that an opening of not over 0.030 inches is suitable. With an opening of this size, the surface tension of the water will normally keep it out, yet the opening is large enough to provide good hearing.

The air column in the auditory canal also exerts a back pressure against water at the fenestration to keep it out.

If desired, a tab 23 can be formed at a suitable location on the exterior surface of the earplug so that the plug can be secured with a leash.

An outstanding feature of the present invention is that it is made of a soft plastic having a density of less than 1. With this density, the plug will float if it falls out of the ear which is a very substantial advantage for swimmers and surfers. One preferred plastic is a styrene-rubber copolymer sold under the trade name Krayton D #2104 and having a durometer softness of 43 A. Naturally the plug can be made of other plastics so long as it is light enough to float and soft enough to be comfortable to the wearer.

I claim:

1. An earplug having thin walls and having an external flange adapted to engage the pinna helix and tragus of the ear and with an inwardly extending conical portion adapted to fit into the concha and outer portion of the auditory canal, terminating in a rectangular knob with a flat substantially solid wall with a small hole in said wall, and with a small flange thereon, said knob sealing off the meatus of the external ear canal without substantially penetrating the external ear canal, said flange anchoring the plug at the entrance of the external ear canal, said plug being made of a soft plastic with a density of less than 1.

2. The plug of claim 1 made of a styrene-rubber copolymer having a durometer hardness of about 43 A.

* * * * *